United States Patent [19]

Beny

[11] Patent Number: 5,253,382
[45] Date of Patent: Oct. 19, 1993

[54] POWER OPERATED TOOTHBRUSH

[76] Inventor: Janos Beny, 1886 Maya Ct., Vista, Calif. 92083

[21] Appl. No.: 938,290

[22] Filed: Aug. 31, 1992

[51] Int. Cl.$^5$ ............................................. A61C 17/34
[52] U.S. Cl. ........................................ 15/22.1; 15/22.2; 74/50; 310/50; 433/216
[58] Field of Search ............... 15/22.1, 22.2; 310/50, 310/80, 83; 74/22 R, 26, 25, 45, 50; 433/216

[56] References Cited

U.S. PATENT DOCUMENTS

| | | | |
|---|---|---|---|
| 2,486,062 | 10/1949 | Ridner | 15/167 |
| 3,159,859 | 12/1964 | Rasmussen | 15/22.1 |
| 3,562,566 | 2/1971 | Kircher | 310/80 |
| 3,699,952 | 10/1972 | Waters et al. | 15/22.1 |
| 3,702,487 | 11/1972 | Sung | 15/22.1 |
| 4,149,291 | 4/1979 | Stoltz | 15/22.1 |
| 4,156,620 | 5/1979 | Clemens | 134/6 |
| 4,175,299 | 11/1979 | Teague | 15/22.1 |
| 4,420,851 | 12/1983 | Wiener | 15/22.1 |
| 4,710,995 | 12/1987 | Joyashiki | 15/22.1 |
| 4,791,945 | 12/1988 | Moriyama | 132/84 |
| 4,974,278 | 12/1990 | Hommann | 15/22.1 |
| 4,995,131 | 2/1991 | Takeda | 15/22.1 |
| 5,020,179 | 4/1991 | Scherer | 15/22.1 |
| 5,027,463 | 7/1991 | Daub | 15/22.1 |
| 5,033,150 | 7/1991 | Gross | 15/22.1 |
| 5,054,149 | 10/1991 | Si-Hoe | 15/28 |

FOREIGN PATENT DOCUMENTS 2838015 3/1979 Fed. Rep. of Germany ....... 15/22.1
1250455 12/1960 France ........................... 15/22.1

Primary Examiner—Edward L. Roberts
Attorney, Agent, or Firm—Poms, Smith, Lande & Rose

[57] ABSTRACT

A power-operated toothbrush for cleaning and stimulating the surface of the teeth, cleaning between the teeth, cleaning between the teeth and gums, and cleaning and stimulating the gums of a user having a housing, a power means, a toothbrush extending from the housing having a bristled toothbrush head and an oscillating or movement imparting means for driving the toothbrush head in a complex motion, such as a figure-eight motion. The brush driving means of the power-operated toothbrush may comprise a rotary motor, a gear element driven by the rotary motor, a cam follower pivotally attached to the motor, and a T-bar. The T-bar is driven in a direction along the longitudinal axis of the power-operated toothbrush housing and also in a direction perpendicular to the longitudinal axis of the power-operated toothbrush housing. The complex motion of the toothbrush head across the surface of the teeth is produced by driving the T-bar to move one cycle in a direction along the longitudinal axis of the housing while simultaneously driving the T-bar to move more than one cycle in a direction perpendicular to the longitudinal axis of the housing. The toothbrush head is preferably driven in a figure-eight motion across the surface of the teeth by driving the T-bar to move two cycles in a direction perpendicular to the longitudinal axis of the housing.

25 Claims, 5 Drawing Sheets

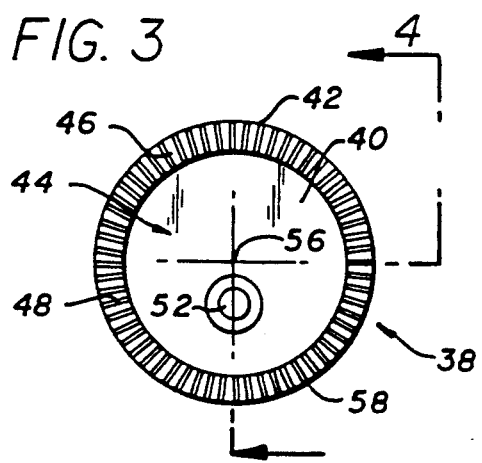
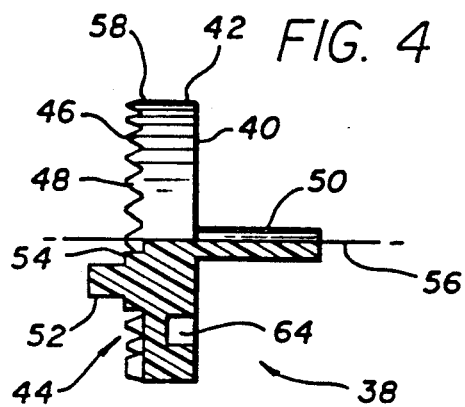
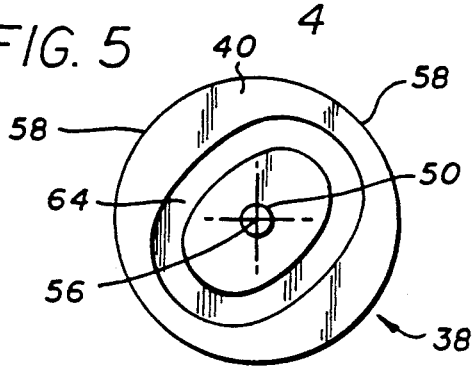
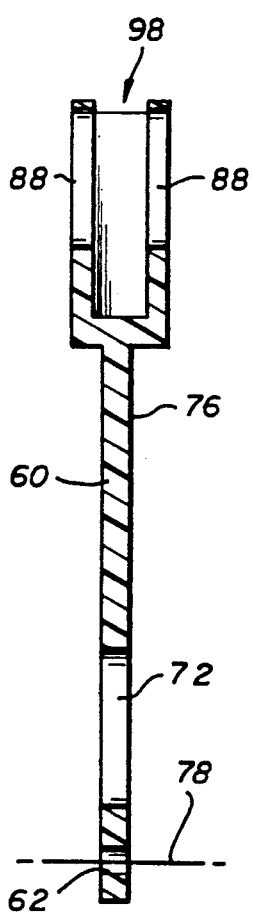
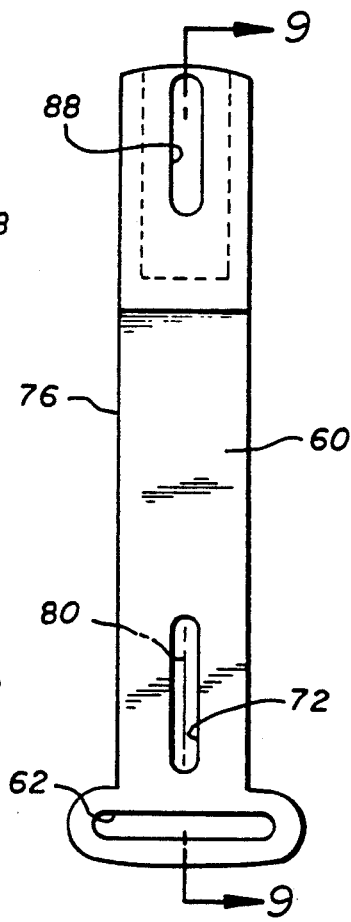
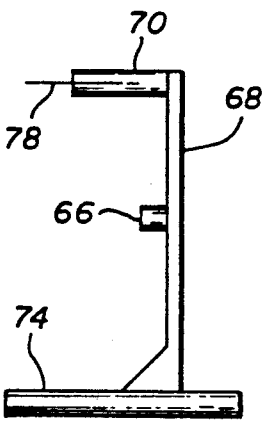
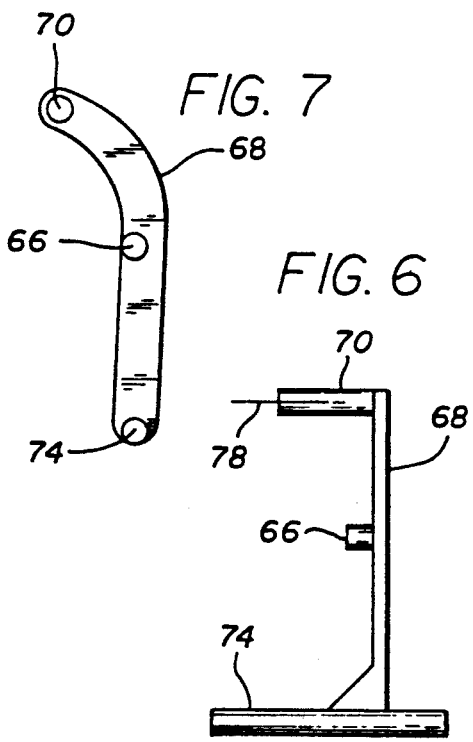

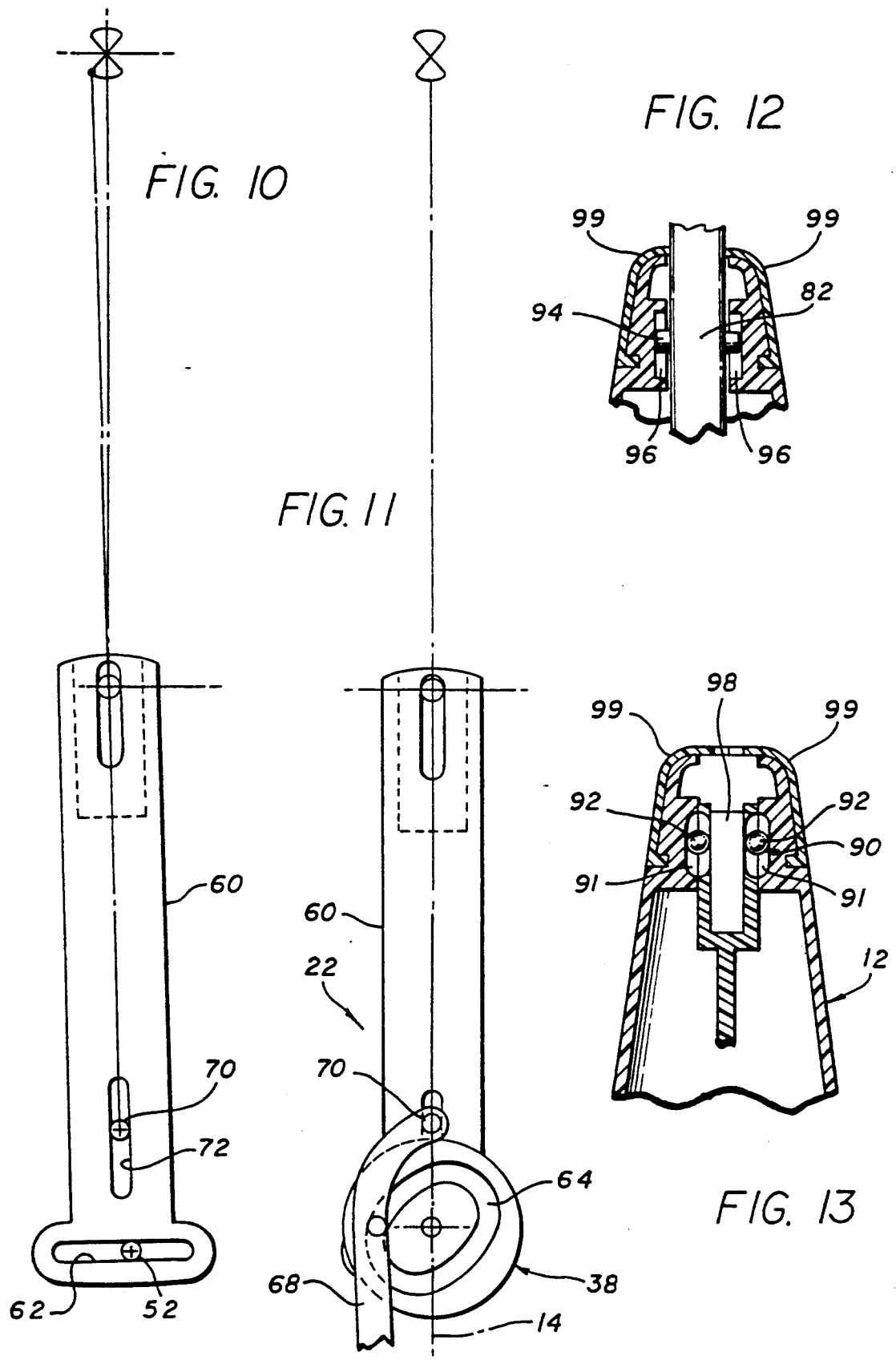

POWER OPERATED TOOTHBRUSH

FIELD OF THE INVENTION

The present invention relates in general to power operated toothbrushes and more particularly to a power operated toothbrush having a toothbrush head that oscillates in a complex motion such as a figure-eight motion.

BACKGROUND OF THE INVENTION

In order to facilitate hygienic care of the teeth and gingival areas, a variety of power operated toothbrushes have been developed and are currently available on the market. Typically, these power operated toothbrushes are electrically driven to drive the toothbrush head in either a linear motion or through a limited rotary motion.

Many types of power operated toothbrushes are well known in the art; however, these power operated toothbrushes have design characteristics that can be improved. For instance, one type of power operated toothbrush provides a linear motion of the toothbrush head. This linear motion of the toothbrush head is an axial back and forth motion, wherein the toothbrush head moves in one direction, stops, and then moves back in the opposite direction, and then repeats this linear motion. When a toothbrush of this type is applied to the surface of the teeth, the bristles of the toothbrush head that are in contact with the teeth will move across the teeth, cleaning the teeth as the toothbrush head moves in one direction. However, when the toothbrush head reaches the end of this motion, the bristles stop on the surface of the teeth, are bent back in the opposite direction, and are brought back across the teeth in the opposite direction. At the point where the bristles stop on the teeth, the cleaning action of the bristles also stops. It is undesirable, in the motion of the toothbrush head across the teeth, that the cleaning bristles should stop, since a regular or continuous cleaning action on the teeth will not be provided.

Another type of power operated toothbrush currently available has a toothbrush head having at least one tuft of bristles rotatably mounted in the toothbrush head. Each rotating tuft of bristles, in combination with a toothpaste, cleans the surface of the teeth, the space between the teeth, the gums, and the space between the teeth and gums. There are however, problems inherent with power operated toothbrushes having rotating tufts of bristles, since abrasive-type toothpastes may build up in the rotating tufts of bristles and cause the rotating tuft of bristles to lock or bind, preventing their rotation.

Accordingly, a principal object of the present invention is to provide a power operated toothbrush that can clean the surface of the teeth, can clean between the teeth, can clean between the teeth and gums, and can clean and stimulate the gums of a user in a more reliable and beneficial way than previously available with automatic toothbrushes.

Another object of the present invention is to provide a power operated toothbrush wherein the bristles of the toothbrush head are continually moving across the surface of the teeth and do not stop while in contact with the surface of the teeth.

A further object of the present invention is to provide a power operated toothbrush wherein the bristles will not lock up or bind when an abrasive toothpaste is used.

Yet another object of the present invention is to provide a power operated toothbrush in which the toothbrush bristles on the head move in a complex motion across the surface of the teeth, such as a figure-eight or cross-over motion, to clean and sweep placque and debris from under the gum line in a forward and reverse arc.

Yet another object of the present invention is to provide a power operated toothbrush having a support means for the toothbrush that moves or oscillates in a direction along the longitudinal axis of the power operated toothbrush housing and also simultaneously moves in a direction perpendicular to the longitudinal axis of the power operated toothbrush housing to produce a complex motion.

It is yet a further object of the present invention to provide a power operated toothbrush wherein the support means for the toothbrush oscillates one cycle in a direction along the longitudinal axis of the housing while simultaneously moving more than one cycle in a direction perpendicular to the longitudinal axis of the housing to produce a complex motion of the toothbrush head across the surface of the teeth.

Another object of the present invention is to provide a power operated toothbrush wherein the support means of the toothbrush oscillates one cycle in a direction along the longitudinal axis of the housing while simultaneously moving two cycles in a direction perpendicular to the longitudinal axis of the housing to cause the toothbrush head to move in a figure-eight or cross-over motion across the surface of the teeth.

Yet another object of the present invention is to provide a power operated toothbrush wherein the shaft supporting the toothbrush bristles oscillates in a direction along the longitudinal axis of the housing or the shaft while simultaneously moving in a direction perpendicular to the longitudinal axis of the housing thus producing two directions of non-circular movement from one drive shaft.

It will be appreciated from the foregoing that there is a definite need for a power operated toothbrush that provides the above objects. The present invention fulfills these needs.

SUMMARY OF THE INVENTION

In accordance with the present invention, a power operated toothbrush is provided that has bristles on a toothbrush head that move in a complex motion such as a figure-eight or cross-over motion, has a constant cleaning action by the bristles on the teeth, and that has bristles whose motion is not locked up by abrasive toothpastes. The foregoing objectives are achieved with a toothbrush having a brush driving means for moving the bristles of the toothbrush head in a complex motion, such as a figure-eight motion, cross-over or other continuous, arcuate shape.

In one preferred embodiment of the present invention, a rotary motor, a gear element driven by the rotary motor, a cam follower pivotally attached to the motor mount, and a toothbrush support bar is provided.

The gear element is preferably a cup gear or face gear. A cup gear is a circular gear having a circular base and circular wall forming a hollow interior. The gear teeth of a cup gear are located on the top edge or lipped surface of the circular wall of the cup gear. The gear element preferably further includes a crank pin. The crank pin extends upwardly from the base of the cup gear to move the brush driving means longitudinally.

The underside of the gear element further includes cam surfaces cut into the outside portion of the base of the gear element to move the brush driver laterally or perpendicular to the longitudinal direction.

The cam follower is pivotally attached to the motor mount and preferably includes a follower pin for contacting the cam surfaces of the gear element and further includes an output pin at the end tip of the cam follower.

A toothbrush support bar or T-bar drives the toothbrush and preferably has an output pin slot for engaging the output pin of the cam follower, a crank pin slot for engaging the crank pin of the gear element, a pivot slot for engaging a pivot pin located within the housing of the power operated toothbrush and a toothbrush slot for engaging and supporting the toothbrush. The toothbrush is any toothbrush having a bristled head shaped to clean the teeth of a user.

The two-dimensional, non-circular movement of the T-bar, produced by one drive element, causes the bristles on the toothbrush head to move in a complex motion. This complex motion is preferably any continuous motion having a lateral component simultaneous with an upward and a downward movement and in one preferred embodiment is a figure-eight or cross-over motion. This motion keeps the bristles of the toothbrush head in a constant or continuous motion on the teeth of the user. Thus, the motion of the bristles provides a constant cleaning action on the teeth of the user, minimizes the possibility of binding when using abrasive tooth pastes and provides an improved cleaning action.

In one preferred embodiment of the present invention, the crank pin of the gear element is placed in such a position on the inside of the base of the gear element and the cam surface is shaped in such a way on the outside of the base of the gear element that when the crank pin causes the T-bar to oscillate one cycle in a direction along the longitudinal axis of the housing, the output pin of the cam follower simultaneously causes the T-bar to move more than one cycle in a direction non-parallel to the longitudinal axis of the housing. In this embodiment, the bristles on the toothbrush head move in the figure-eight or cross-over motion described above. In another preferred embodiment of the present invention, the crank pin causes the T-bar to oscillate one cycle in a direction along the longitudinal axis of the housing, while the output pin simultaneously causes the T-bar to move two cycles in a direction substantially perpendicular to the longitudinal axis of the housing. In this embodiment, the bristles on the toothbrush head move in a figure-eight motion.

In another preferred embodiment of the present invention, a rotary motor, a first gear element driven by the rotary motor, a second gear element driven by the first gear element, and a toothbrush support means is provided. Thus, the complex motion, or preferably the figure-eight motion of the toothbrush head may be achieved by the use of a first and second gear element combination.

It is apparent that the power operated toothbrush of the present invention has a toothbrush head that moves in a complex motion, such as a figure-eight motion which will not lock up when an abrasive toothpaste is used. The toothbrush of the present invention can be used with any type of toothpaste. The bristles of the power operated toothbrush of the present invention are in a substantially continuous motion on the surface of the teeth of the user to provide an improved and constant cleaning action by the bristles on the teeth of the user in forward and reverse arcuate motion under the gum line.

Other objects, features and advantages of the invention will become apparent from a consideration of the following detailed description and from the accompanying drawings.

BRIEF DESCRIPTION OF THE DRAWINGS

FIG. 3 is a top view of a gear element for use with the invention shown in FIG. 1;

FIG. 4 is a side and partial sectional view of the gear element taken along line 4—4 of FIG. 3;

FIG. 5 is a top plan view of the gear element of the present invention showing the cam surface;

FIG. 6 is a side elevation view of a cam follower for use with the toothbrush of FIG. 1;

FIG. 7 is a top view of the cam follower of FIG. 6;

FIG. 8 is a top plan view of a T-bar for use with the toothbrush shown in FIG. 1;

FIG. 9 is a side-sectional view of the T-bar taken along the line 9—9 in FIG. 8;

FIG. 10 is a top view of the T-bar of FIG. 8 and a crank pin, output pin and pivot pin and depicting graphically the figure-eight motion of the toothbrush head;

FIG. 11 is a bottom view of the T-bar, gear element, and cam follower with the figure-eight motion of the toothbrush head indicated graphically;

FIG. 12 is an enlarged cross-sectional view of a further embodiment of a pivot point for the T-bar showing a pivot pin fixed to the T-bar for confined movement in a pivot pin slot of the housing;

FIG. 13 is a partial cross-sectional view of a toothbrush slot and rolling ball pivot according to a further embodiment of the present invention;

DETAILED DESCRIPTION OF THE PREFERRED EMBODIMENTS

The present invention is embodied in a power operated toothbrush having bristles on a toothbrush head that move in a complex motion, such as a cross-over or figure-eight motion, providing a constant cleaning action by the bristles on the teeth of the user and whose motion are not locked up by abrasive toothpastes. The power operated toothbrush is suited for cleaning and stimulating the teeth, cleaning between the teeth, cleaning between the teeth and the gums, and cleaning the gums of the user.

Figure 14:
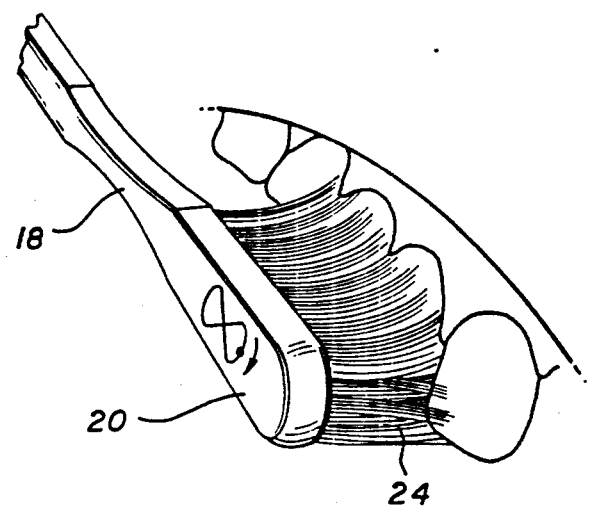
FIG. 14 is an elevational view showing the toothbrush head on the surface of the teeth of the user with the arrow and graphic figure-eight indicating the figure-eight motion of the toothbrush head.

In one particular embodiment shown in the drawings and herein described, a power operated toothbrush 10 (see FIGS. 1 and 2) is provided. The power operated toothbrush comprises a hollow housing 12, having a longitudinal axis 14, a power means 16, a toothbrush 18 having a bristled head 20 extending from the housing and having a brush driving means for moving the bristles of the toothbrush head 20 on the teeth of the user. (See FIG. 14). The hollow housing 12 is preferably formed from a plastic or metal and has a shape allowing it to be comfortably gripped by the user for manipulating the toothbrush head on the teeth of the user. The power means 16 is preferably any form of replaceable or rechargeable batteries and are preferably of a AA size, or the power source may be line power. The toothbrush 18, extending from the housing, is preferably formed from a plastic material and has a conventional bristled toothbrush head 20 shaped to fit easily within the mouth and clean the surface of the teeth, between the teeth, between the teeth and gums, and the gums of the user. The bristles 24 of the toothbrush may be of any stiffness depending on the preference and needs of the user.

In one preferred embodiment of the present invention, a rotary motor 26 (FIGS. 1 and 2) is provided which is preferably any electrically driven motor which produces a rotary motion in a rotating drive shaft 28. The rotary motor is switched on and off by a switch 30 accessible at the surface of the housing 12. Any vibrations of the rotary motor 26 are reduced by rubber shock absorbers 32 between the motor 26 and the housing 12. Attached to the end of the rotating drive shaft 28 is a motor pinion 34 having gear teeth 36 around its circumference.

The rotary motor drives a transmission or gear element 38 preferably to impart at least one portion of the brush movement to the brush. (See FIGS. 1, 2, 3-5, and 11). The gear element 38 is preferably a cup gear having a circular base 40 and circular wall 42 around the circumference of the base 40 forming a hollow interior 44. The gear teeth 46 of the gear element 38 are located on the top edge 48 or lipped surface of the circular wall 42 of the gear element 38. The gear teeth 36 of the motor pinion 34 engage the gear teeth 46 of the gear element 38 to rotate the gear element 38 around its gear shaft 50. The gear element may also be any other type of gear such as a face gear or a bevel gear as is well-known in the art.

The gear element 38 preferably has a crank pin 52 for imparting longitudinal movement to the brush. The crank pin 52 extends from the inside portion of the base 40 from a wider pedestal 54 which terminates at the level of the upper edge 48 of the circular wall 42 of the gear element 38. The crank pin 52 is located on a radius of the gear element between the center 56 of the gear element 38 and the circumference 58 of the gear element 38. The location of the crank pin 52 in its distance from the center 56 of the gear element 38 determines in part the amplitude of longitudinal oscillation of the T-bar 60 as the crank pin 52 moves the T-bar 60 by the crank pin slot 62, as discussed infra.

The gear element 38 preferably has cam surfaces 64 cut into the outside of the base 40 to impart transverse movement to the brush. The cam surfaces 64 generally form an elliptical shape about the center of the gear element. The gear shaft 50 preferably extends from the center 56 of the elliptical shape. The cam surfaces 64 have a width sufficient to engage the follower pin 66 of the cam follower 68, as discussed infra. The shape of the cam surfaces 64 is particularly significant as this shape determines the amplitude and frequency of transverse movement of the T-bar 60 as the output pin 70 of the cam follower 68 moves within the output pin slot 72 of the T-bar 60 as discussed infra.

The relative dimensions of the major and minor axes of the ellipse shown in FIG. 5 are to scale and produce the described substantially figure-eight motion shown in the drawings. As would be apparent to those skilled in the art, there is an imaginary circle defining a static circle (not shown) which, if followed exactly by the follower pin 66, would result in no lateral movement of the brush. Any cam surfaces outside the static circle result in brush movement to one side of a center longitudinal axis of the brush, and any cam surfaces inside result in movement to the other side of the center. With cam surfaces forming an elliptical shape having dimensions such that the ellipsis crosses the static circle four times, the brush bristles cross the longitudinal axis four times. Alternatively, the cam surfaces could be such as to produce a "dumb-bell" or "dual-lobed" shape which produces multiple lateral movement at the same time as the longitudinal movement. Other shapes can be produced.

The cam surfaces may be formed as a groove in a flat surface guiding the follower pin 66 or as an upstanding wall guiding a pair of spaced apart follower pins. Those skilled in the art can devise other equivalent structures to achieve the functions of transmitting the circular motion of the gear element 38 to lateral and longitudinal movement of the brush, such as in the form of cam surfaces, cranks, combinations of cam surfaces and cranks, or other elements.

The cam follower 68 (FIGS. 1, 2, 6, 7 and 11) preferably has a pivot pin 74 at one end for pivotally mounting the cam follower 68 to the motor mount. The cam follower 68 preferably has a follower pin 66 that engages and follows the cam surfaces 64 of the gear element 38. As the gear element 38 rotates, the follower pin 66 follows the cam surfaces 64 of the gear element 38 causing the cam follower 68 to pivot, thereby moving the follower pin 66 in a complex motion, as defined by the moving cam surface 64. The pivoting of the cam follower 68 causes the output pin 70 of the cam follower 68 extending upwardly from the tip of the cam follower 68 to move the T-bar 60 through the output pin slot 72, as discussed infra.

The T-bar 60, in the preferred embodiment, provides a mount or receptacle for the brush and drives the brush through action of the gear 38 and motor 26 (FIGS. 1, 2, and 9-11). The T-bar converts or translates the rotational motion of the gear to the complex motion imparted to the brush by way of the output pin slot 72 for engaging the output pin 70 of the cam follower 68 and the crank pin slot 62 for engaging the crank pin 52 of the gear element 38. The longitudinal axis 78 of the crank pin slot is preferably perpendicular to the longitudinal axis 14 of the housing 12 and the longitudinal axis 80 of the output pin slot 72 is preferably parallel to or along the longitudinal axis 14 of the housing 12.

In this embodiment of the present invention, the toothbrush head 20 moves in the following manner. As the gear element 38 rotates, the crank pin 52 pushes the crank pin slot 62 of the T-bar 60 causing the T-bar 60 to move in a direction along the longitudinal axis 14 of the housing 12. (See FIGS. 1-11). Simultaneously, the output pin 70 pushes the output pin slot 72 of the T-bar 60 thereby causing the end of the T-bar 60 to move in a direction substantially perpendicular to the longitudinal axis 14 of the housing 12 about a pivot point.

Figure 1:
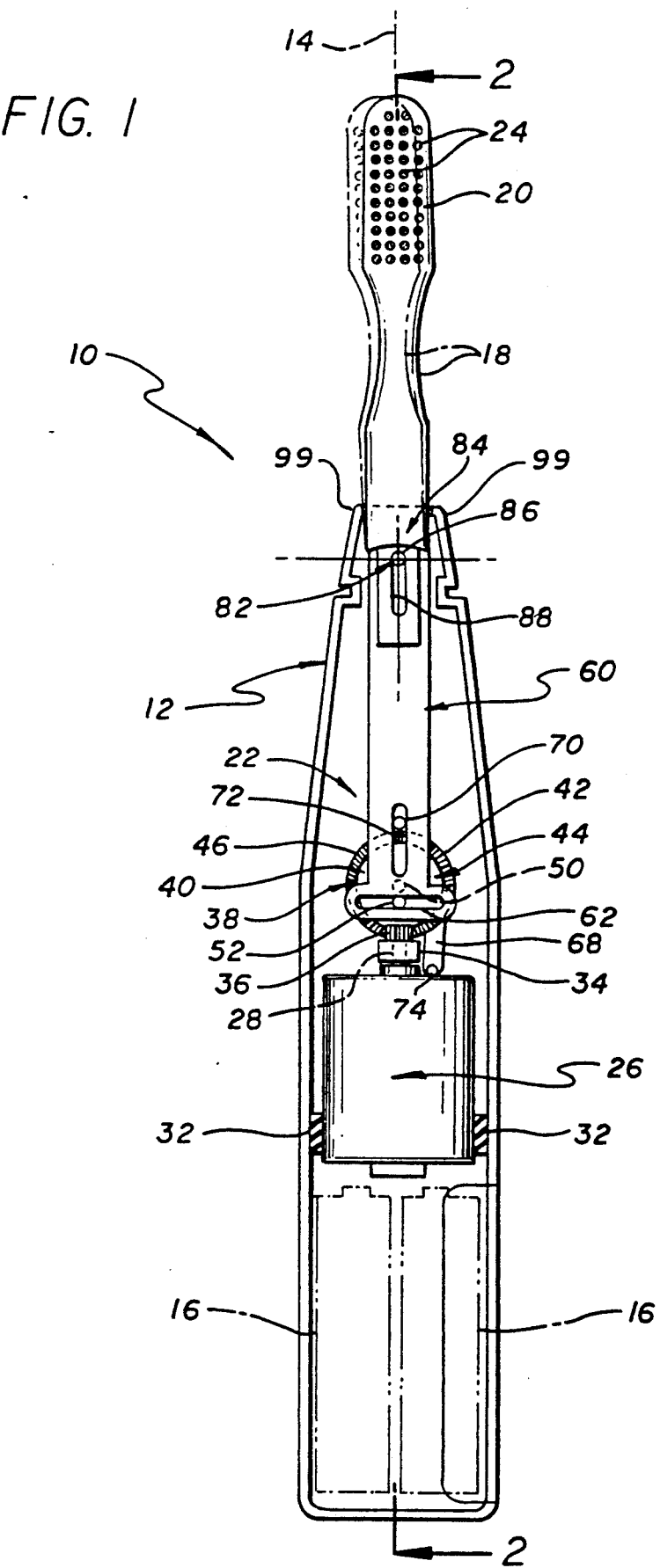
FIG. 1 is a longitudinal cross-sectional top view showing a toothbrush with a brush driving mechanism according to which one aspect of the present invention can be used.
Figure 2:
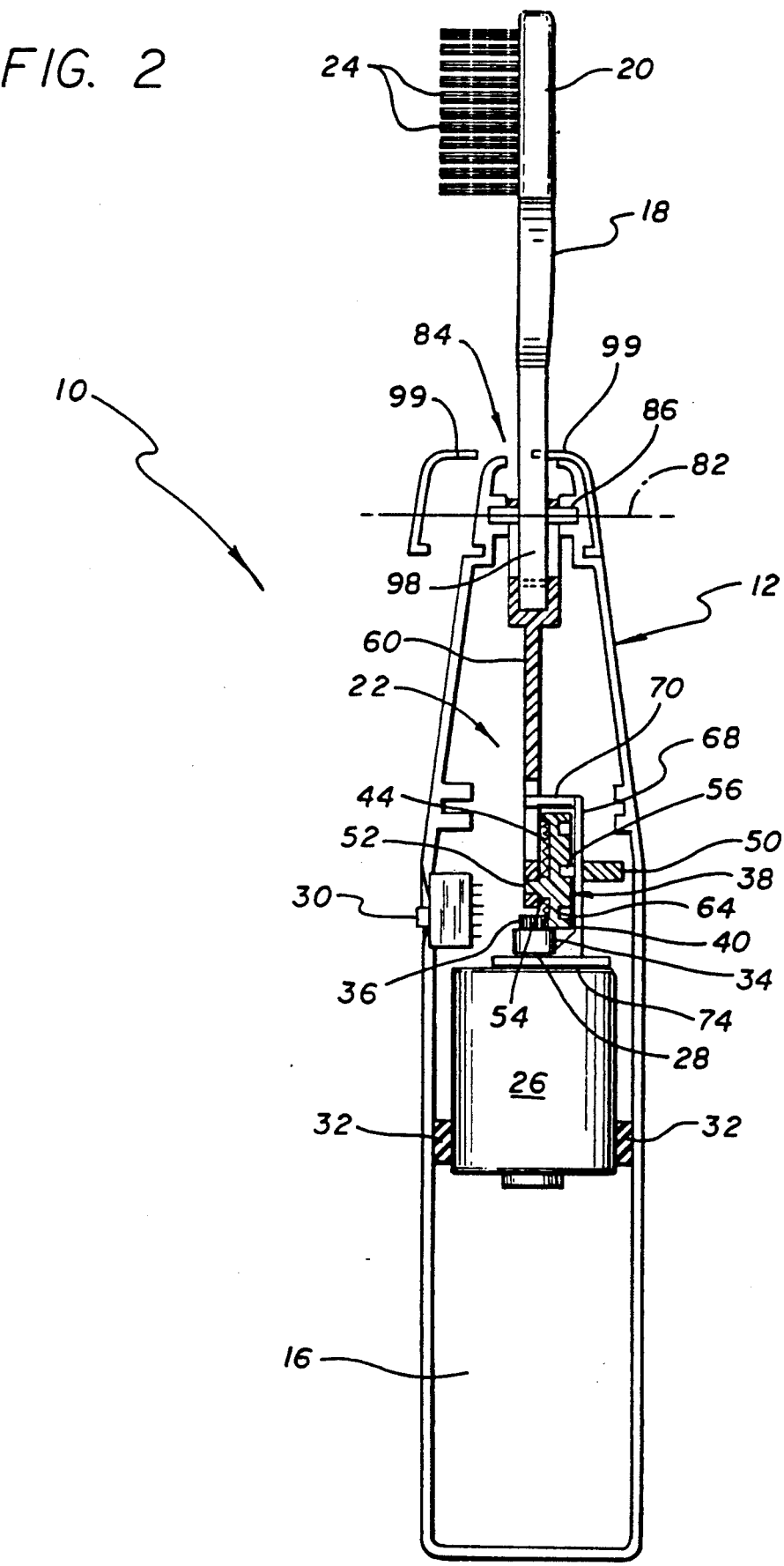
FIG. 2 is a longitudinal cross-sectional side view taken along the line 2—2 in FIG. 1 showing the power operated toothbrush of the present invention.

The T-bar 60 slides about a pivot point 82 near the opening 84 of the housing 12. This pivot point 82 is preferably a fixed pivot pin 86 passing through a pivot pin slot 88 on the T-bar 60. (See FIGS. 1 and 2). In another preferred embodiment of the present invention, the pivot point may be defined by a rolling ball pivot 90 (FIG. 13) wherein one pair of ball bearings 92 are each located within a respective rolling ball recess 91 within the housing 12 of the toothbrush and corresponding recesses in the T-bar 60. In another preferred embodiment of the present invention, the pivot point 82 may be defined by a pin 94 on the T-bar 60 that moves within a pair of recessed pivot slots 96 in the housing 12 (FIG. 12). The embodiments of the pivot shown in FIGS. 1, 2 and 13 establish a pivot point on the bar which is movable relative to the body of the toothbrush. In FIGS. 1 and 2, for example, the distance from the output pin 70, moving the end of the T-bar, to the pivot point on the T-bar changes as the T-bar is pushed back and forth. Therefore, the precise path followed by brush bristles is not precisely symmetrical unless the cam surfaces or other mechanism for driving the T-bar end laterally are suitably adjusted.

The T-bar preferably includes a conventional toothbrush slot 98 or other suitable receptacle for reliably engaging and supporting an automatic toothbrush 18. (See FIGS. 1, 2 and 9). The toothbrush slot 98 is a slot that frictionally engages the end of the toothbrush 18. The toothbrush slot 98 provides a connection for the toothbrush 18 so that the toothbrush 18 may be removed and replaced with a new one when the bristles become worn. A rubber boot 99 is provided around the opening 84 of the housing 12 that surrounds the toothbrush 18 to seal the interior of the housing 12 (shown split section to show the connection, for clarity).

As mentioned above, the position of the crank pin 52 and the shape of the cam surfaces 64 are significant in determining the motion of the toothbrush head 20. (See FIGS. 1-11). The crank pin 52 is preferably located in a position on the gear element 38 and the cam surfaces 64 are likewise preferably shaped such that, when the crank pin 52 moves with the gear element, e.g., oscillates, the T-bar 60 moves one cycle in a direction along the longitudinal axis 14 of the housing 12, and, when the output pin 70 pushes the output pin slot 72 of the T-bar 60, the T-bar 60 simultaneously moves more than one cycle in a direction substantially perpendicular to the longitudinal axis 14 of the housing 12, thus causing the toothbrush head 20 to follow a complex though continuous motion.

The complex motion is preferably any continuous motion having an undulation, for example. As can be seen in the context of the figure-eight motion, the toothbrush bristles follow a left-to-right lateral component while simultaneously following two vertical components, one up and one down. The same occurs with the right-to-left lateral component. Therefore, in the preferred embodiment, each lateral component simultaneously has both an up and a down component. This preferred bristle motion provides better cleaning on and between the teeth and under the gums. However, the path need not be a complete or a symmetrical figure-eight. The path could follow a plurality of arcs or curvatures, even of different radii. However, it is preferred to have a rising and falling (vertical component) motion in one lateral direction and a rising and falling motion in the other lateral direction, resulting, for example, in a clockwise rising then falling arcuate motion in one lateral direction and a counterclockwise rising then falling arcuate motion in the other lateral direction. This continuous motion, without any stopping to reverse direction, provides a better cleaning action for the teeth, especially in areas relatively inaccessible with present automatic toothbrushes. The use of the standard bristle brush head with continuous motion permits use of any standard toothpaste without binding.

In a preferred embodiment of the present invention, the placement of the crank pin 52 and the shape of the cam surface are such that the movement of the crank pin causes the T-bar 60 to move one cycle in a direction along the longitudinal axis 14 of the housing 12 while the movement of the output pin causes the T-bar 60 to simultaneously move two cycles in a direction perpendicular to the longitudinal axis 14 of the housing 12 thereby causing the toothbrush head 20 to follow in a figure-eight motion. (See, FIGS. 10, 11 and 14).

Figure 15:
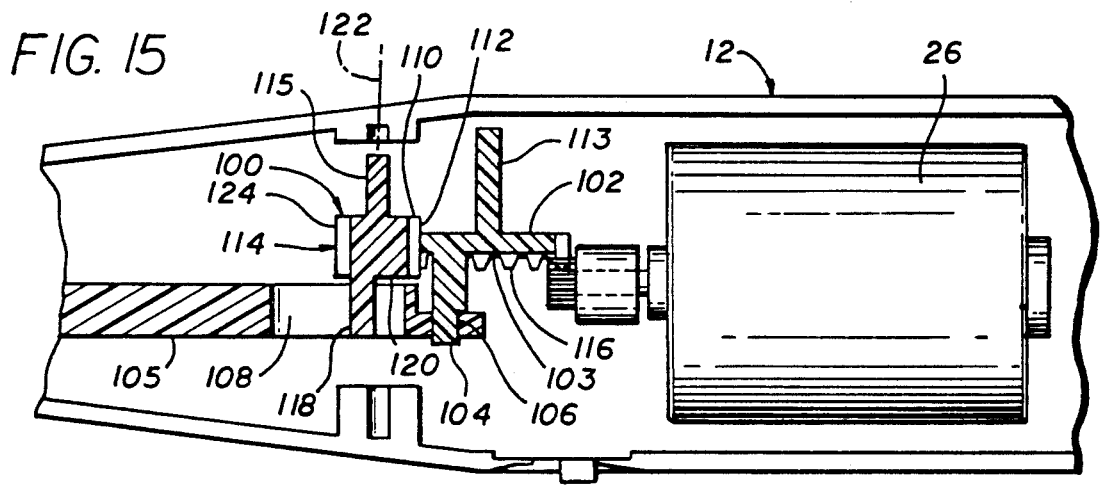
FIG. 15 is a partial side section view of one embodiment of the power operated toothbrush showing first and second gear elements.
Figure 16:
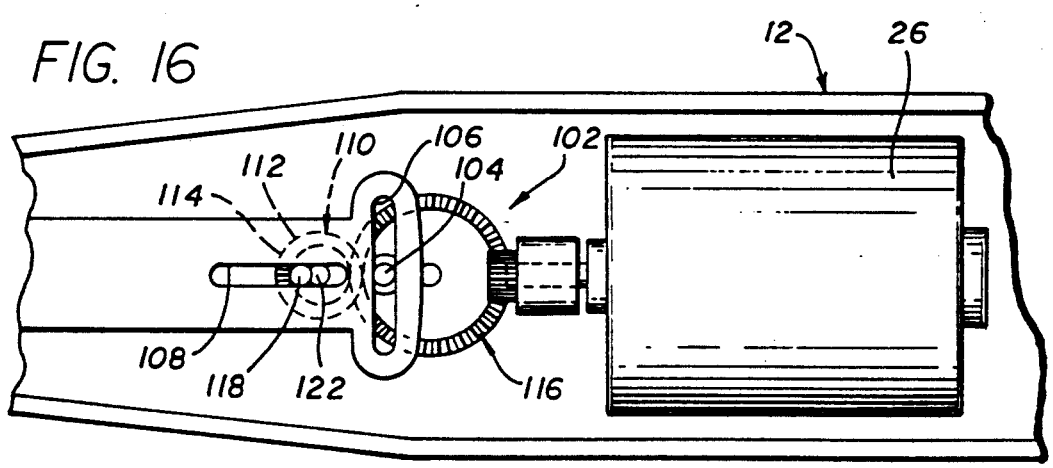
FIG. 16 is a partial top sectional view of the embodiment of the power operated toothbrush shown in FIG. 15.

In another preferred embodiment of the present invention, a second gear element 100 (FIGS. 15 and 16) is driven by a first gear element 102. The first gear element has a first crank pin 104 extending from the inside of the base 103 of the gear element. In this embodiment of the present invention, the toothbrush support means is a T-bar 105 as in the previously described embodiment of the present invention having a first crank pin slot 106 and a second crank pin slot 108. The second gear element 100 is preferably a spur gear having its gear teeth 110 located on the outer circumferential surface 112 of the circular wall 114 of the second gear element 110 being engaged with the gear teeth 116 of the first gear element 102. The second gear element 100 has a second crank pin 118 extending from the inside of the base 120 of the second gear element and being in a position on a radius of the second gear element between the center 122 of the second gear element 100 and the circumference 124 of the second gear element 100.

In this embodiment of the present invention, the toothbrush head preferably moves in the following manner. The rotary motor 26 rotates the rotating gear shaft 128 to rotate the first gear element 102 around its gear shaft 113 and thereby rotate the second gear element about its gear shaft 115. Thus, the first crank pin 104 pushes the first crank pin slot 106 causing the T-bar 105 to move in a direction along the longitudinal axis 114 of the housing 112 while the second crank pin simultaneously pushes the second crank pin slot 108 causing the T-bar 105 to move in a direction relatively perpendicular to the longitudinal axis 14 of the housing 12.

In this embodiment of the present invention, the first and second crank pins 104 and 118, respectively, of the first and second gear elements, are preferably placed in a position such that the first crank pin 104 pushes the first crank pin slot 106 of the T-bar 105 to cause the T-bar 105 to move one cycle in a direction along the longitudinal axis 14 of the housing 12 while the second crank pin 118 of the second gear element 100 pushes the second crank pin slot 108 of the T-bar 105 to cause the T-bar 105 to move more than one cycle in a direction relatively perpendicular to the longitudinal axis 14 of the housing 12. This movement of the T-bar 105 causes the toothbrush head 20 to move in the complex motion described above.

In yet another preferred embodiment of the present invention, the first and second crank pins, 104 and 118, respectively, are each located in a position where the T-bar 105 moves one cycle in a direction along the longitudinal axis 14 of the housing 12 while the T-bar 105 simultaneously moves 14 two cycles in a direction perpendicular to the longitudinal axis 14 of the housing 12. This movement of the T-bar 105 causes the toothbrush head 20 to move in a figure-eight motion. (See FIG. 14).

Thus, it can be seen that both preferred embodiments of the present invention provide a power operated toothbrush that can clean the surface of the teeth, can clean between the teeth, can clean between the teeth and gums, and can clean and stimulate the gums of the user. The power operated toothbrush of the present invention has a toothbrush head that moves in a complex motion, preferably a figure-eight motion. The bristles of the toothbrush head provide a constant cleaning action on the teeth and gums of the user, since the bristles are constantly moving in a complex motion, preferably a figure-eight motion, on the surface of the tooth and gums of the user rather than in a start-stop mode. The power operated toothbrush of the present invention can be used with any type of toothpaste without the bristles or the mechanism of the toothbrush head binding.

While a particular form of the invention has been illustrated and described, it will be apparent that various modifications can be made without departing from the scope of the invention. For instance, in the embodiment of the invention containing a first gear element 102 and a second gear element 100, the first crank pin slot 106 of the T-bar may be substituted with a wire engaged at one end to the first crank pin 104 and at the other end to the T-bar 105 at a point near the pivot pin slot 88 for imparting translational movement of the T-bar 105 in a direction along the longitudinal axis 14 of the housing 12. Moreover, while the brush has been described as moving the bristles in a plane such that the path of the bristles in the complex motion lies in a plane, the invention is not limited to such. Accordingly, it is not intended that the invention be limited by the specific embodiment disclosed in the drawings and described in detail hereinabove.

I claim:

1. A power operated toothbrush comprising:
    a hollow housing having a longitudinal axis;
    a power means;
    a toothbrush extending from the housing and having a bristled toothbrush head;
    a means for driving the toothbrush head in a figure-eight motion.

2. A power operated toothbrush as defined in claim 1, wherein the toothbrush includes a guide surface and the driving means includes a pivot pin inside the housing for contacting the guide surface for defining part of the motion of the toothbrush head.

3. A power operated toothbrush as defined in claim 2, wherein the toothbrush head driving means comprises:
    a rotary motor;
    a gear element driven by the rotary motor, the gear element having a crank pin and a cam surface;
    a cam follower for pivoting relative to the gear element, the cam follower having a follower pin in contact with the cam surfaces of the gear element and having an output pin; and
    a bar having an output pin slot for engaging the output pin of the cam follower, a crank pin slot for engaging the crank pin of the gear element, a pivot slot for engaging the pivot pin of the housing and a toothbrush slot for engaging the toothbrush.

4. A power operated toothbrush as defined in claim 2, wherein the toothbrush head driving means comprises:
    a rotary motor;
    a first gear element driven by the rotary motor, the first gear element having a first crank pin;
    a second gear element driven by the first gear element, the second gear element having a second crank pin; and
    a bar having an first crank pin slot for engaging the first crank pin, a second crank pin slot for engaging the second crank pin, a pivot slot for engaging the pivot pin of the housing and a toothbrush slot for engaging the toothbrush.

5. The power operated toothbrush of claim 1 wherein the means for driving the toothbrush head in the figure-eight motion drives the toothbrush head such that the head moves longitudinally one cycle for every two cycles of lateral movement.

6. A power operated toothbrush comprising:
    a hollow housing having an opening and having a longitudinal axis;
    a toothbrush support means located within the housing;
    means connected to the support means and mounted within the housing for imparting translational movement to the support means along the longitudinal axis of the housing and for imparting translational movement to the support means perpendicular to the longitudinal axis of the housing, wherein while the movement imparting means moves one cycle in a direction along the longitudinal axis of the housing, the movement imparting means simultaneously moves more than one cycle in a direction substantially nonparallel to the longitudinal axis of the housing;
    power means operatively connected to the movement imparting means; and
    a toothbrush connected to the toothbrush support means and extending through the opening of the housing, the toothbrush having a bristled head, the toothbrush head moving in a complex motion by the movement of the support means.

7. A power operated toothbrush as defined in claim 6, wherein while the movement imparting means moves one cycle in a direction along the longitudinal axis of the housing, the movement imparting means simultaneously moves two cycles in a direction perpendicular to the longitudinal axis of the housing, thereby causing the toothbrush head to move in a substantially figure-eight motion.

8. A power operated toothbrush as defined in claim 6, wherein the toothbrush support means is a bar having a slot for engaging the housing.

9. A power operated toothbrush as defined in claim 8, wherein the housing includes a pivot pin located within the housing and wherein the slot includes a pivot pin slot on the bar wherein the pivot pin is engaged through the pivot pin slot.

10. A power operated toothbrush as defined in claim 9, wherein the movement imparting means comprises a gear element having a cam surface and a crank pin, the gear element being driven by a rotary motor, and comprising a cam follower pivotally attached to the motor mount, the cam follower having a follower pin coupled to the cam surface of the gear element and having an output pin.

11. A power operated toothbrush as defined in claim 10, wherein the bar further includes a crank pin slot for engaging the crank pin and further includes an output pin slot for engaging the output pin.

12. A power operated toothbrush as defined in claim 11, wherein the crank pin pushes the crank pin slot causing the bar to move in a direction along the longitudinal axis of the housing and the output pin pushes the output pin slot causing the bar to move in a direction substantially perpendicular to the longitudinal axis of the housing and wherein while the crank pin moves in a circular path one cycle, the output pin simultaneously moves more than one cycle, thereby causing the toothbrush head to oscillate in a complex motion 13. A power operated toothbrush as defined in claim 11, wherein the crank pin pushes the crank pin slot causing the bar to move in a direction along the longitudinal axis of the housing and the output pin pushes the output pin slot causing the T-bar to move in a direction substantially perpendicular to the longitudinal axis of the housing and wherein while the crank pin moves one cycle, the output pin simultaneously moves two cycles, thereby causing the toothbrush head to move in a figure-eight motion.

14. A power operated toothbrush as defined in claim 10, wherein the gear element is a cup gear.

15. A power operated toothbrush as defined in claim 9, wherein the movement imparting means comprises a first gear element having a first crank pin, the first gear element being driven by a rotary motor and a second gear element having a second crank pin, the second gear element being driven by the first gear element.

16. A power operated toothbrush as defined in claim 15, wherein the bar further includes a first crank pin slot for engaging the first crank pin and further includes a second crank pin slot for engaging the second crank pin.

17. A power operated toothbrush as defined in claim 16, wherein the first crank pin pushes the first crank pin slot causing the bar to move in a direction along the longitudinal axis of the housing and the second crank pin pushes the second crank pin slot causing the bar end to move in a direction substantially perpendicular to the longitudinal axis of the housing and wherein while the first crank pin moves one cycle, the second crank pin moves more than one cycle thereby causing the toothbrush head to move in a complex motion.

18. A power operated toothbrush as defined in claim 16, wherein the first crank pin pushes the first crank pin slot causing the bar to move in a direction along the longitudinal axis of the housing and the second crank pin pushes the second crank pin slot causing a portion of the bar to move in a direction substantially perpendicular to the longitudinal axis of the housing and wherein while the first crank pin moves one cycle, the second crank pin moves two cycles, thereby causing the toothbrush head to move in a figure-eight motion.

19. A power operated toothbrush as defined in claim 15, wherein the first gear element and the second gear element are cup gears.

20. A power operated toothbrush comprising:
a hollow housing having a pivot pin and having a longitudinal axis;
a power source;
a rotary motor;
a gear element driven by the rotary motor, the gear element having a crank pin and a cam surface;
a cam follower pivotally attached to the housing, the cam follower having a follower pin in contact with the cam surface of the gear element and an output pin;
a bar having an output pin slot for engaging the output pin of the cam follower, a crank pin slot for engaging the crank pin of the gear element, a pivot slot for engaging the pivot pin of the housing and a toothbrush slot; and
a toothbrush engaged to the toothbrush slot of the bar.

21. A power operated toothbrush as defined in claim 20, wherein the crank pin pushes the crank pin slot causing the bar to move in a direction along the longitudinal axis of the housing and the output pin pushes the output pin slot causing a portion of the bar to move in a direction perpendicular to the longitudinal axis of the housing and wherein when the crank pin moves one cycle, the output pin moves more than one cycle, thereby causing the toothbrush head to move in a complex motion.

22. A power operated toothbrush as defined in claim 20, wherein the crank pin pushes the crank pin slot causing the bar to move in a direction along the longitudinal axis of the housing and the output pin pushes the output pin slot causing the bar to move in a direction perpendicular to the longitudinal axis of the housing and wherein when the crank pin moves one cycle, the output pin oscillates two cycles thereby causing the bristles of the toothbrush head to move in a figure-eight motion.

23. A power operated toothbrush comprising:
a hollow housing having a pivot pin and having a longitudinal axis;
a power source;
a rotary motor;
a first gear element driven by the rotary motor, the first gear element having a first crank pin;
a second gear element driven by the first gear element, the second gear element having a second crank pin;
a bar having an first crank pin slot for engaging the first crank pin, a second crank pin slot for engaging the second crank pin, a pivot slot for engaging the pivot pin of the housing and a toothbrush slot; and
a toothbrush engaged to the toothbrush slot of the bar.

24. A power operated toothbrush as defined in claim 23, wherein the first crank pin pushes the first crank pin slot causing the bar to move in a direction along the longitudinal axis of the housing and the second crank pin pushes the second crank pin slot causing the bar to move in a direction perpendicular to the longitudinal axis of the housing and wherein when the first crank pin moves one cycle, the second crank pin moves more than one cycle thereby causing the toothbrush head to move in a complex motion.

25. A power operated toothbrush as defined in claim 23, wherein the first crank pin pushes the first crank pin slot causing the bar to move in a direction along the longitudinal axis of the housing and the second crank pin pushes the second crank pin slot causing the bar to move in a direction perpendicular to the longitudinal axis of the housing and wherein when the first crank pin moves one cycle, the second crank pin moves two cycles thereby causing the toothbrush head to move in a figure-eight motion.

* * * * *